US008881365B2

(12) United States Patent
Kuppurathanam et al.

(10) Patent No.: US 8,881,365 B2
(45) Date of Patent: Nov. 11, 2014

(54) IMPLANTABLE GRAFT DEVICE HAVING TREATED YARN AND METHOD FOR MAKING SAME

(75) Inventors: Shyam S V Kuppurathanam, Bloomington, IN (US); Sean D. Chambers, Bloomington, IN (US); David P. Biggs, Bloomington, IN (US); Scott E. Eells, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 2 days.

(21) Appl. No.: 13/457,949

(22) Filed: Apr. 27, 2012

(65) Prior Publication Data

US 2012/0211120 A1  Aug. 23, 2012

Related U.S. Application Data

(62) Division of application No. 12/343,325, filed on Dec. 23, 2008, now Pat. No. 8,187,316.

(60) Provisional application No. 61/016,989, filed on Dec. 27, 2007.

(51) Int. Cl.
*B23P 11/00* (2006.01)
*A61F 2/89* (2013.01)
*A61F 2/07* (2013.01)
*A61F 2/06* (2013.01)

(52) U.S. Cl.
CPC ... *A61F 2/07* (2013.01); *A61F 2/89* (2013.01); *A61F 2002/075* (2013.01); *A61F 2002/065* (2013.01); *A61F 2250/0067* (2013.01)
USPC ............... 29/439; 139/36; 623/1.13

(58) Field of Classification Search
CPC ............ A61F 2002/065; A61F 2/07; A61F 2250/0067; A61F 2002/075; A61F 2/89
USPC ............... 29/439; 139/36; 623/1.13
See application file for complete search history.

(56) References Cited

U.S. PATENT DOCUMENTS

| | | | |
|---|---|---|---|
| 3,304,557 A | 2/1967 | Polansky | |
| 4,670,286 A | 6/1987 | Nyilas et al. | |
| 5,178,630 A | 1/1993 | Schmitt | |
| 5,197,977 A | 3/1993 | Hoffman, Jr. et al. | |
| 5,217,493 A | 6/1993 | Raad et al. | |
| 5,236,447 A * | 8/1993 | Kubo et al. | 623/1.13 |
| 5,599,321 A | 2/1997 | Conway et al. | |
| 5,653,746 A | 8/1997 | Schmitt | |
| 5,733,327 A | 3/1998 | Igaki et al. | |
| 5,824,037 A | 10/1998 | Fogarty et al. | |
| 5,843,158 A | 12/1998 | Lenker et al. | |
| 5,976,179 A | 11/1999 | Inoue | |
| 6,045,568 A | 4/2000 | Igaki et al. | |
| 6,153,252 A * | 11/2000 | Hossainy et al. | 427/2.3 |
| 6,159,239 A | 12/2000 | Greenhalgh | |
| 6,164,339 A | 12/2000 | Greenhalgh | |

(Continued)

*Primary Examiner* — Jermie Cozart
*Assistant Examiner* — Ruth G Hidalgo-Hernande
(74) *Attorney, Agent, or Firm* — Brinks Gilson & Lione

(57) ABSTRACT

An implantable graft device having treated yarn is disclosed. The device comprises a graft body forming a lumen defining a longitudinal axis and comprising proximal and distal ends. The graft body comprises a woven fabric having warp yarns aligned in a first direction and a weft yarns aligned in a second direction. At least one of the weft yarns and the warp yarns has an agent applied thereto defining treated yarns of the graft body.

10 Claims, 4 Drawing Sheets

(56) References Cited

U.S. PATENT DOCUMENTS

| | | |
|---|---|---|
| 6,200,335 B1 | 3/2001 | Igaki |
| 6,346,492 B1 | 2/2002 | Koyfman |
| 6,387,122 B1 | 5/2002 | Cragg |
| 6,395,021 B1 | 5/2002 | Hart et al. |
| 6,485,524 B2 | 11/2002 | Strecker |
| 6,547,820 B1 | 4/2003 | Staudenmeier |
| 6,663,667 B2 | 12/2003 | Dehdashtian |
| 6,685,736 B1 | 2/2004 | White et al. |
| 6,805,706 B2 | 10/2004 | Solovay et al. |
| 6,814,754 B2 | 11/2004 | Greenhalgh |
| 6,849,088 B2 | 2/2005 | Dehdashtian et al. |
| 6,881,221 B2 | 4/2005 | Golds |
| 7,063,721 B2 | 6/2006 | Takahashi et al. |
| 7,122,052 B2 | 10/2006 | Greenhalgh |
| 7,185,597 B1 | 3/2007 | Phillips et al. |
| 2002/0042644 A1 | 4/2002 | Greenhalgh |
| 2002/0156522 A1 | 10/2002 | Ivancev et al. |
| 2003/0229389 A1 | 12/2003 | Escano |
| 2004/0209538 A1 | 10/2004 | Klinge et al. |
| 2004/0215320 A1 | 10/2004 | Machek |
| 2005/0008763 A1 | 1/2005 | Schachter |
| 2005/0149173 A1 | 7/2005 | Hunter et al. |
| 2005/0154446 A1 | 7/2005 | Phillips et al. |
| 2005/0240261 A1 | 10/2005 | Rakos et al. |
| 2005/0273155 A1* | 12/2005 | Bahler et al. .................. 623/1.13 |
| 2005/0283224 A1 | 12/2005 | King |
| 2006/0009835 A1* | 1/2006 | Osborne et al. .............. 623/1.13 |
| 2006/0020328 A1 | 1/2006 | Tan |
| 2006/0142840 A1 | 6/2006 | Sherry et al. |
| 2006/0280775 A1* | 12/2006 | Ashammakhi et al. ........ 424/426 |
| 2008/0175885 A1 | 7/2008 | Asgari |
| 2008/0228028 A1 | 9/2008 | Carlson et al. |
| 2009/0171435 A1 | 7/2009 | Kuppurathanam et al. |
| 2009/0171451 A1 | 7/2009 | Kuppurathanam et al. |
| 2010/0063576 A1 | 3/2010 | Schaeffer et al. |

* cited by examiner

IMPLANTABLE GRAFT DEVICE HAVING TREATED YARN AND METHOD FOR MAKING SAME

CROSS-REFERENCE TO RELATED APPLICATIONS

This patent application is a divisional of co-pending U.S. patent application Ser. No. 12/343,325, filed on Dec. 23, 2008, which application claims the benefit of U.S. Provisional Application Ser. No. 61/016,989, filed on Dec. 27, 2007, entitled "IMPLANTABLE GRAFT DEVICE HAVING TREATED YARN AND METHOD FOR MAKING SAME," the entire contents of which are incorporated herein by reference.

BACKGROUND OF THE INVENTION

The present invention relates generally to an improved vascular graft and method for bridging a defect in a main vessel near one or more branch vessels.

Aneurysms occur in blood vessels in locations where, due to age, disease or genetic predisposition, the blood vessel strength or resiliency is insufficient to enable the blood vessel wall to retain its shape as blood flows therethrough, resulting in a ballooning or stretching of the blood vessel at the limited strength/resiliency location to thereby form an aneurysmal sac. If the aneurysm is left untreated, the blood vessel wall may continue to expand, to the point where the remaining strength of the blood vessel wall is below that necessary to prevent rupture, and the blood vessel will fail at the aneurysm location, often with fatal result.

To prevent rupture, a stent graft of a tubular construction may be introduced into the blood vessel, for example intraluminally. Typically, the stent graft is deployed and secured in a location within the blood vessel such that the stent graft spans the aneurysmal sac. The outer surface of the stent graft, at its opposed ends, is sealed to the interior wall of the blood vessel at a location where the blood vessel wall has not suffered a loss of strength or resiliency. Blood flow in the vessel is thus channeled through the hollow interior of the stent graft, thereby reducing, if not eliminating, any stress on the blood vessel wall at the aneurysmal sac location. Therefore, the risk of rupture of the blood vessel wall at the aneurysmal location is significantly reduced, if not eliminated, and blood can continue to flow through to the downstream blood vessels without interruption.

Although adequate, a stent graft may undesirably become occluded once implanted within an abdominal aorta of a patient to gradually obstruct the lumen of the stent or create thrombosis. Moreover, after implantation of the device, the modulation of haemocompatability, inflammation or protease activity may undesirably become an issue. The lack of haemocompatability may lead to the patient's immune system becoming activated to attack foreign cells and creating blood clots. Additionally, undesirable inflammation causes swelling of the vessels and uncontrollable protease activity may affect the breakdown of clots that form in vessels.

BRIEF SUMMARY OF THE INVENTION

Examples of the present invention generally provide methods of making implantable devices having a reduced risk of obstruction and an improved capability of modulating conditions such as hemocompatability, inflammation, and protease activity. In one embodiment, the present invention provides a stent graft device made of yarn that is treated with an agent and is configured to provide improved modulation of haemocompatability, inflammation, or protease activity. Thus, for example, if haemocompatability is a patient's issue, then the agent will affect protease activity to improve the breakdown of clots that form in area of implantation. The agents used may also be an anti-inflammatory agent to reduce the possibility of swelling of the vessels due to a patient's haemocompatability condition.

In one example, the present invention provides a method for making an implantable graft device having treated yarn. The method comprises applying an agent on at least one of weft yarns and warp yarns and drying the at least one of the weft and warp yarns. The method further comprises interlacing the warp yarns in a first direction with the weft yarns in a second direction to define a graft body having a lumen defining a longitudinal axis and comprising proximal and distal ends.

In another example, the present invention provides an implantable graft device having treated yarn. The device comprises a graft body forming a lumen defining a longitudinal axis and comprising proximal and distal ends. The graft body comprises a woven fabric having warp yarns aligned in a first direction and weft yarns aligned in a second direction. At least one of the weft yarns and the warp yarns has an agent applied thereto defining treated yarns of the graft body.

In another example, the present invention provides an implantable graft device having treated yarn. The device comprises a graft body forming a lumen defining a longitudinal axis and comprising proximal and distal ends. The graft body comprises a woven fabric having warp yarns aligned in a first direction and weft yarns aligned in a second direction. At least one of the weft yarns and the warp yarns has an agent applied thereto defining treated yarns of the graft body. The device further comprises an expandable stent disposed circumferentially on the graft body and about the longitudinal axis. The device further comprises an anchor portion extending from the proximal end of the graft body. The anchor portion has a first woven portion and a barb stent attached thereto for reduced migration of the graft device. The first woven portion is comprised of woven yarn. The device further comprises an end portion extending from the distal end of the graft body. The end portion has a second woven portion and an end stent attached thereto. The second woven portion is comprised of woven yarn.

Further objects, features, and advantages of the present invention will become apparent from consideration of the following description and the appended claims when taken in connection with the accompanying drawings.

BRIEF DESCRIPTION OF THE DRAWINGS

FIG. 1b is an enlarged view of the device in FIG. 1a;

DETAILED DESCRIPTION OF THE INVENTION

Figure 1A:
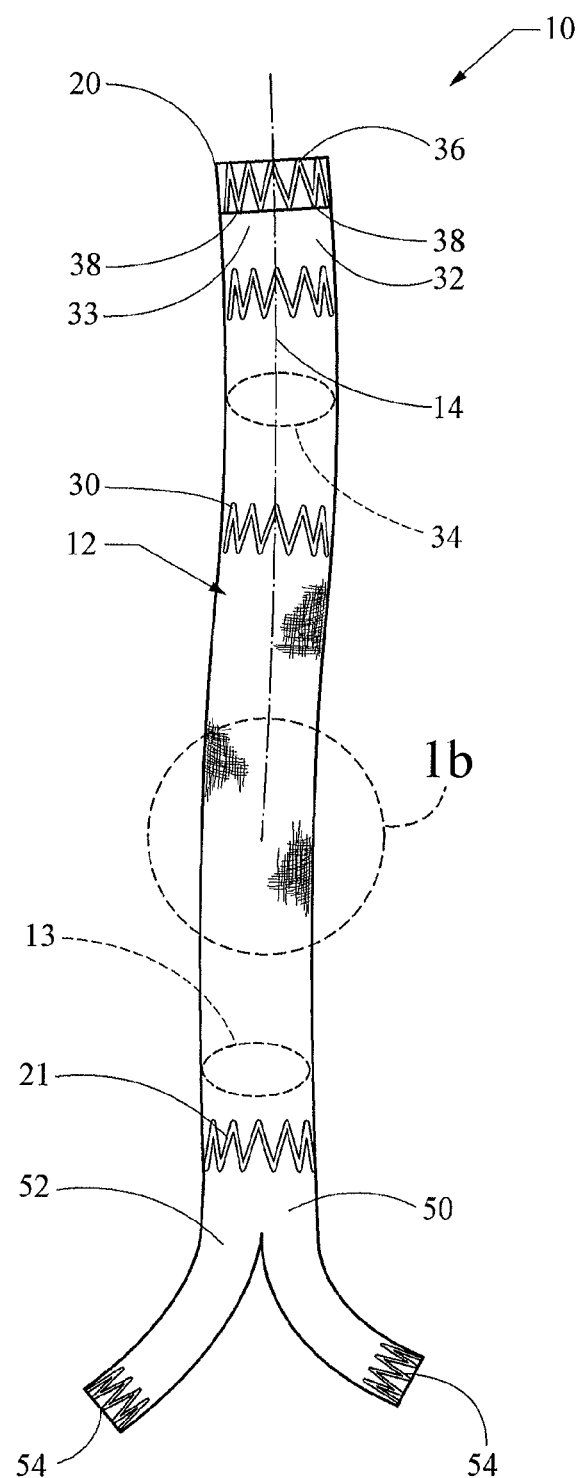
FIG. 1a is a side view of an implantable graft device having treated yarn in accordance with one embodiment of the present invention.

Embodiments of the present invention provide implantable graft devices having treated yarn and methods of making such devices. The devices comprise woven fabric having warp yarns aligned in a first direction and weft yarns aligned in a second direction, wherein at least one of the weft yarns or the warp yarns has an agent applied thereon defining treated yarns of the graft body.

Unless otherwise defined, all technical and scientific terms used herein have the same meaning as commonly understood by one of ordinary skill in the art to which this invention pertains. In case of conflict, the present document, including definitions, will control. Preferred methods and materials are described below, although methods and materials similar or equivalent to those described herein can be used in the practice or testing of the present invention. All publications, patent applications, patents and other references mentioned herein are incorporated by reference in their entirety. The materials, methods, and examples disclosed herein are illustrative only and not intended to be limiting.

The term "implantable" refers to an ability of a medical device to be positioned at a location within a body, such as within a body lumen.

As used herein, the term "body vessel" means any tube-shaped body passage lumen that conducts fluid, including but not limited to blood vessels such as those of the human vasculature system, esophageal, intestinal, billiary, urethral and ureteral passages.

The term "branch vessel" refers to a vessel that branches off from a main vessel. The "branch vessels" of the thoracic and abdominal aorta include the celiac, inferior phrenic, superior mesenteric, lumbar, inferior mesenteric, middle sacral, middle suprarenal, renal, internal spermatic, ovarian (in the female), innominate, left carotid, and left subclavian arteries. As another example, the hypogastric artery is a branch vessel to the common iliac, which is a main vessel in this context. Thus, it should be seen that "branch vessel" and "main vessel" are relative terms.

The terms "about" or "substantially" used with reference to a quantity includes variations in the recited quantity that are equivalent to the quantity recited, such as an amount that is insubstantially different from a recited quantity for an intended purpose or function.

The term "stent" means any device or structure that adds rigidity, expansion force, or support to a prosthesis.

The term "stent graft" as used herein refers to a prosthesis comprising a stent and a graft material associated therewith that forms a lumen through at least a portion of its length.

The term "biocompatible" refers to a material that is substantially non-toxic in the in vivo environment of its intended use, and that is not substantially rejected by the patient's physiological system (i.e., is non-antigenic). This can be gauged by the ability of a material to pass the biocompatibility tests set forth in International Standards Organization (ISO) Standard No. 10993 and/or the U.S. Pharmacopeia (USP) 23 and/or the U.S. Food and Drug Administration (FDA) blue book memorandum No. G95-1, entitled "Use of International Standard ISO-10993, Biological Evaluation of Medical Devices Part-1: Evaluation and Testing." Typically, these tests measure a material's toxicity, infectivity, pyrogenicity, irritation potential, reactivity, hemolytic activity, carcinogenicity and/or immunogenicity. A biocompatible structure or material, when introduced into a majority of patients, will not cause a significantly adverse, long-lived or escalating biological reaction or response, and is distinguished from a mild, transient inflammation which typically accompanies surgery or implantation of foreign objects into a living organism.

Figure 1B:
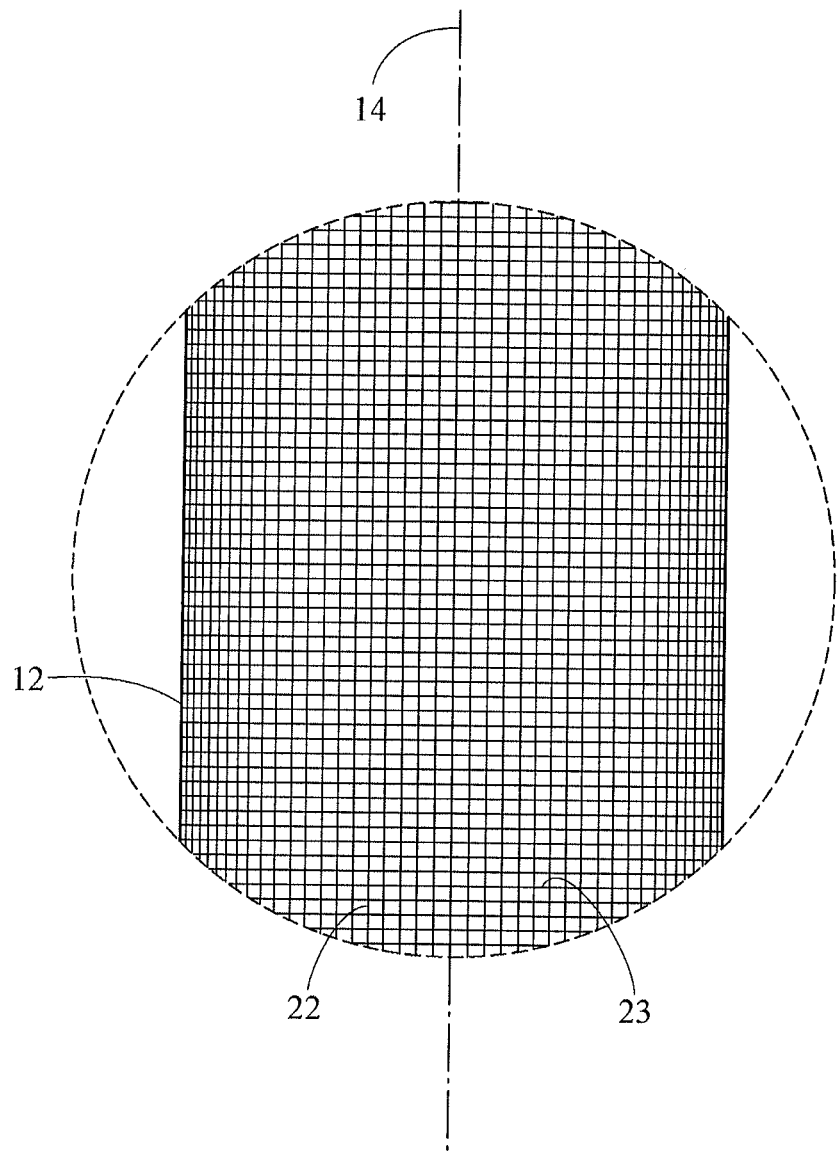

FIG. 1 illustrates an implantable graft device 10 having treated yarn in accordance with one embodiment of the present invention. As shown, the device 10 comprises a graft body 12 forming a lumen 13 defining a longitudinal axis 14 and comprising proximal and distal ends 20, 21. The graft body 12 may be any prosthesis that is introduced temporarily or permanently into the patient's body for the prophylaxis or therapy of a medical condition. Typical subjects (also referred to herein as "patients") are vertebrate subjects (i.e., members of the subphylum cordata), including, mammals such as cattle, sheep, pigs, goats, horses, dogs, cats and humans. In this embodiment, the graft body 12 comprises a woven fabric having warp yarns 22 aligned in a first direction and weft yarns 23 aligned in a second direction. Preferably, the warp yarns 22 are the lengthwise threads attached to a loom before weaving begins. The weft yarns 23 (also known as woof or fill yarns) are the yarns that are shuttled back and forth across the warp yarns, defining the woven fabric. Each of the warp and weft yarns 22, 23 may be threads of spun fibre. The fibre may be comprised of a various material (discussed in greater detail below).

Preferably a plurality of weft yarns or warp yarns, or at least one, have a first agent applied thereto defining treated yarns of the graft body. The first agent may include any suitable agent for treatment while the device is implanted in the anatomy of a patient, e.g., an anti-microbial agent, an anti-thrombogenic agent, an anti-inflammatory agent, a biologically active compound, a biomaterial, an extracellular matrix (e.g., small intestine submucosa gel), or a bio-absorbable material. In this embodiment, at least some of the weft yarn or some of the warp yarn are comprised of a first strand and a second strand. Preferably, the first or second strand comprises the first agent which has been applied thereto. In this example, the combination or multitude of twisted strands defines each fibre of yarns.

In this embodiment, the device 10 further comprises an expandable stent 30 disposed circumferentially on the graft body 12 and about the longitudinal axis. The stent 30 may be attached circumferentially about the graft body 12 by any suitable means such as by sewing or adhesive or sonic bonding.

Preferably, the device 10 further comprises an anchor portion 32 attached to the proximal end 20 of the graft body 12 and extends proximally therefrom. The anchor portion 32 has a first woven portion 33 comprised of woven yarn. As shown, the first woven portion 33 comprises an inner side 34. In this embodiment, the anchor portion 32 further has a barb stent 36 comprising a plurality of loops 38 attached to the first woven portion 33. As shown, the barb stent 36 is attached to the inner side 34 of the woven portion 33 for reduced migration of the graft device 10. In this embodiment, the device 10 includes an end portion 50 extending from the distal end 21 of the graft body 12. The end portion 50 has a second woven portion 52 comprised of woven yarn and an end stent 54 attached thereto.

The first agent is one of a biologically active compound, a biomaterial, an antimicrobial agent, an extracellular matrix (e.g., small intestine submucosa gel), and a bio-absorbable material. Preferably, the term "antimicrobial agent" refers to a bioactive agent effective in the inhibition of, prevention of or protection against microorganisms such as bacteria, microbes, fungi, viruses, spores, yeasts, molds and others generally associated with infections such as those contracted from the use of the medical articles described herein. The antimicrobial agents include antibiotic agents and antifungal agents. The antimicrobial agent may include one of the following: cephaloporins, clindamycin, chlorampheanicol, carbapenems, minocyclines, rifampin, penicillins, monobactams, quinolones, tetracycline, macrolides, sulfa antibiotics, trimethoprim, fusidic acid and aminoglycosides. Antifungal agents include amphotericin B, azoles, flucytosine, cilofungin and nikko Z. Moreover, bactericidal nitrofuran compounds, such as those described by U.S. Pat. No. 5,599,321 (Conway et al.), incorporated herein by reference, can also be used as antimicrobials.

Examples of suitable antimicrobial materials include nano-size particles of metallic silver or an alloy of silver containing about 2.5 wt % copper (hereinafter referred to as "silver-copper"), salts such as silver citrate, silver acetate, silver benzoate, bismuth pyrithione, zinc pyrithione, zinc percarbonates, zinc perborates, bismuth salts, various food preservatives such as methyl, ethyl, propyl, butyl, and octyl benzoic acid esters (generally referred to as parabens), citric acid, benzalkonium chloride (BZC), rifamycin and sodium percarbonate. In each process, single or multiple kinds of antimicrobial agents may be used.

Specific non-limiting examples of suitable antibiotic agents include: ciprofloxacin, doxycycline, amoxicillin, metronidazole, norfloxacin (optionally in combination with ursodeoxycholic acid), ciftazidime, and cefoxitin. Other suitable antibiotic agents include rifampin, minocycline, novobiocin and combinations thereof discussed in U.S. Pat. No. 5,217,493 (Raad et al.). Rifampin is a semisynthetic derivative of rifamycin B, a macrocyclic antibiotic compound produced by the mold *Streptomyces mediterranic*. Rifampin is believed to inhibit bacterial DNA-dependent RNA polymerase activity and is bactericidal in nature. Rifampin is available in the United States from Merrill Dow Pharmaceuticals, Cincinnati, Ohio. Minocycline is a semisynthetic antibiotic derived from tetracycline. It is primarily bacteriostatic and is believed to exert an antimicrobial effect by inhibiting protein synthesis. Minocycline is commercially available as the hydrochloride salt which occurs as a yellow, crystalline powder and is soluble in water and slightly soluble in alcohol. Minocycline is available from Lederle Laboratories Division, American Cyanamid Company, Pearl River, N.Y. Novobiocin is an antibiotic obtained from cultures of *Streptomyces niveus* or *S. spheroides*. Novobiocin is usually bacteriostatic in action and is believed to interfere with bacterial cell wall synthesis and inhibit bacterial protein and nucleic acid synthesis. Novobiocin also appears to affect stability of the cell membrane by complexing with magnesium. Novobiocin is available from The Upjohn Company, Kalamazoo, Mich.

Bactericidal nitrofuran compounds, such as those described by U.S. Pat. No. 5,599,321 (Conway et al.), incorporated herein by reference, can also be used as an antimicrobial bioactive agent. Preferred nitrofuran bioactive agents include nitrofurantoin, nitrofurazone, nidroxyzone, nifuradene, furazolidone, furaltidone, nifuroxime, nihydrazone, nitrovin, nifurpirinol, nifurprazine, nifuraldezone, nifuratel, nifuroxazide, urfadyn, nifurtimox, triafur, nifurtoinol, nifurzide, nifurfoline, nifuroquine, and derivatives of the same, and other like nitrofurans which are both soluble in water and possess antibacterial activity. References to each of the above cited nitrofuran compounds may be found in the Merck Index, specifically the ninth edition (1976) and the eleventh edition (1989) thereof, published by Merck & Co., Inc., Rahway, N.J., the disclosures of which are each incorporated herein by reference.

Another example of a suitable antimicrobial agent is described in published U.S. patent application US2005/0008763A1 (filed Sep. 23, 2003 by Schachter), incorporated herein by reference in its entirety.

It is also to be understood that the antithrombogenic agent mentioned above may include any suitable antithrombogenic agent known in the art to reduce thrombus formation about the device while in a body vessel of a patient. Examples of antithrombotic bioactive agents include anticoagulants such as heparin, phosphorylcholine, low molecular weight heparin, covalent heparin, synthetic heparin salts, coumadin, bivalirudin (hirulog), hirudin, argatroban, ximelagatran, dabigatran, dabigatran etexilate, D-phenalanyl-L-poly-L-arginyl, chloromethy ketone, dalteparin, enoxaparin, nadroparin, danaparoid, vapiprost, dextran, dipyridamole, omega-3 fatty acids, vitronectin receptor antagonists, DX-9065a, CI-1083, JTV-803, razaxaban, BAY 59-7939, and LY-51, 7717; antiplatelets such as eftibatide, tirofiban, orbofiban, lotrafiban, abciximab, aspirin, ticlopidine, clopidogrel, cilostazol, dipyradimole, nitric oxide sources such as sodium nitroprussiate, nitroglycerin, S-nitroso and N-nitroso compounds; fibrinolytics such as alfimeprase, alteplase, anistreplase, reteplase, lanoteplase, monteplase, tenecteplase, urokinase, streptokinase, or phospholipid encapsulated microbubbles; and other bioactive agents such as endothelial progenitor cells or endothelial cells.

Figure 2:
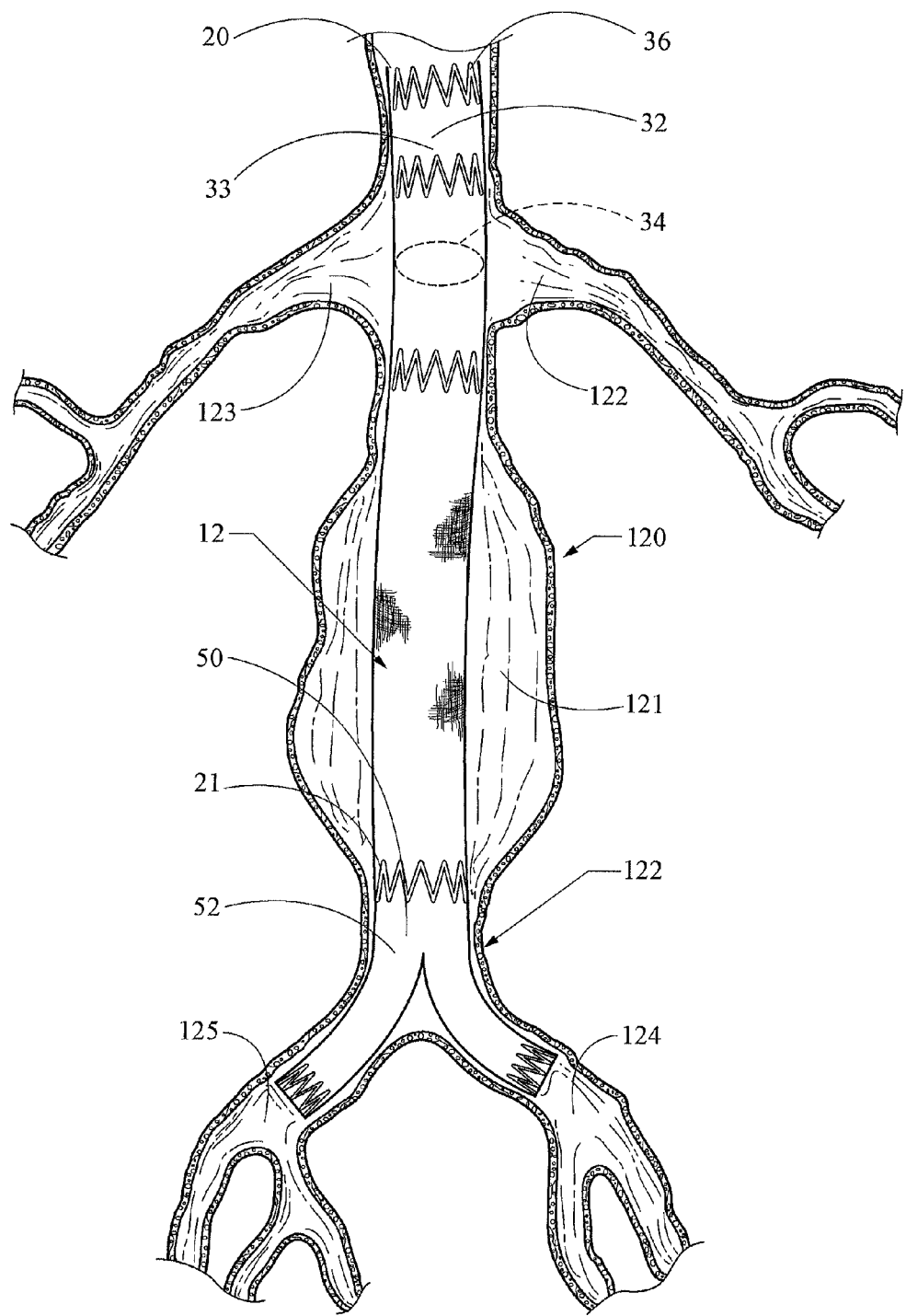
FIG. 2 is an environmental view of the implantable graft device of FIG. 1.

FIG. 2 illustrates the graft device 10 implanted within renal arteries 122, 123 and the arteries 124, 125 in accordance with one embodiment of the present invention. The aorta 120 has an aneurysm 121 between the renal arteries 122, 123 and the iliac arteries 124, 125. Upon implantation, the agent(s) applied on the yarns of the graft device 10 may begin an eluting process or time-delayed eluting process. Though the above embodiments illustrate grafts located within the aorta, prostheses of the present invention may be implanted in any body vessel, including main vessels in which one or more branch vessels may be located.

Figure 3:
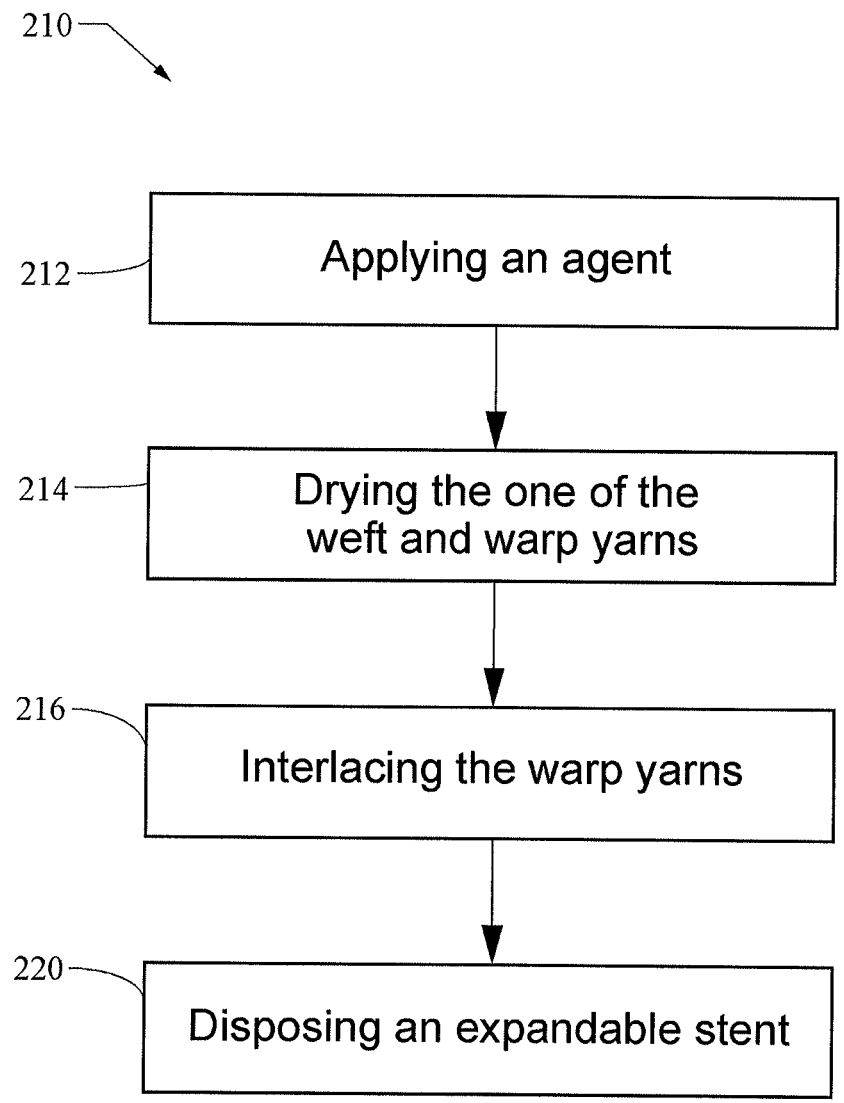
FIG. 3 is a flow chart of one method for making an implantable graft device having treated yarn in accordance with another example of the present invention.

FIG. 3 is a flow chart depicting a method 210 of making an implantable graft device having treated yarn in accordance with one example of the present invention. In this example, the method comprises applying in box 212 an agent (discussed above) on at least one of weft yarns or warp yarns. This may be accomplished by any suitable process such as by dipcoating, spray coating, plasma deposition, chemical vapor deposition, vapor deposition, and chemical attachment.

The method further comprises drying in box 214 the weft and warp yarns and interlacing in box 216 the warp yarns in a first direction with the weft yarns in a second direction to define a graft body having a lumen defining a longitudinal axis and comprising proximal and distal ends. Preferably the first direction is substantially parallel to the longitudinal axis and the second direction is perpendicular to the longitudinal axis. In this example, the warp yarns or the weft yarns comprise first and second yarns, wherein one of the first and second yarns comprises the first agent applied thereto. The first and second yarns are then combined together to define the weft yarns or the warp yarns.

The method further comprises attaching or disposing in box 220 an expandable stent circumferentially on the graft body and about the longitudinal axis. As discussed above, the graft body includes an anchor portion and an end portion, defining the implantable graft device. A barb stent is then attached to the anchor portion for reduced migration of the graft device. This may be accomplished by attaching the ends of the stent about the end portion.

Graft Weaves

The graft may comprise any kind of suitable weave or weaves. For example, the graft body may include, but is not limited to, weaves such as plain weaves, modified plain weaves, basket weaves, rep or rib weaves, twill weaves (e.g., straight twill, reverse twill, herringbone twill), modified twill weaves, satin weaves, double weaves (e.g., double-width, tubular double weave, reversed double weave), and any other related weaves. In one embodiment, the graft body comprises a plain weave having 150 ends per inch and 250 picks per inch. An "end" refers to an individual warp yarn, and "sett" is the number of warp yarns per inch in a woven fabric. A "pick"

refers to an individual weft yarn, and "pick count" is the number of weft yarns per inch in a woven fabric.

Graft Material

The graft material may comprise any biocompatible material suitable for weaving. The graft material may be natural, synthetic, or manufactured. For example, biocompatible materials include, but are not limited to, polyesters, such as poly(ethylene terephthalate); fluorinated polymers, such as polytetrafluoroethylene (PTFE) and fibers of expanded PTFE; and polyurethanes. In addition, materials that are not inherently biocompatible may be subjected to surface modifications in order to render the materials biocompatible. Examples of surface modifications include graft polymerization of biocompatible polymers from the material surface, coating of the surface with a crosslinked biocompatible polymer, chemical modification with biocompatible functional groups, and immobilization of a compatibilizing agent such as heparin or other substances. Thus, any fibrous material may be used to form a graft body, provided the final textile is biocompatible.

Polymeric materials suitable for weaving graft material include polyethylene, polypropylene, polyaramids, polyacrylonitrile, nylons and cellulose, in addition to polyesters, fluorinated polymers, and polyurethanes as listed above. Desirably, the graft body material comprises one or more polymers that do not require treatment or modification to be biocompatible. More desirably, the graft body material comprises biocompatible polyesters. Even more desirable, graft body material comprises polyethylene terephthalate and PTFE. A preferred commercial example of polyethylene terephthalate especially suitable for weaving is Dacron™. These materials are relatively inexpensive, easy to handle, have good physical characterstics and are suitable for clinical application.

The graft material may be woven of a single material or combination of materials. Determination of which combination of materials woven in which direction of the graft body that is most appropriate may be based on the type of clinical application, properties of the graft body that are desired, and further factors such as the weave type, yarn properties such as the size or denier of the yarn, finishing techniques, and/or permeability of the textile. For example, for percutaneous application, thin graft body are preferred. Such thin grafts comprise yarns that have are fine or have a low denier. Desirably, graft body yarns range in size from about 0.1 denier to about 200 denier.

Stents

One or more stents may be attached or adhered to the graft body by any means known to one skilled in the art, including but not limited to welding, stitching, bonding, and adhesives. In one preferred embodiment, stents may be sutured to the graft body. In general, stents for use in accordance with the present invention typically comprise a plurality of apertures or open spaces between metallic filaments (including fibers and wires), segments or regions. Typical structures include: an open-mesh network comprising one or more knitted, woven or braided metallic filaments; an interconnected network of articulable segments; a coiled or helical structure comprising one or more metallic filaments; and, a patterned tubular metallic sheet (e.g., a laser cut tube).

In one embodiment, stents are located distal and proximal to the graft body. For example, as shown in FIG. 1, stent 36 is located on the proximal end of the graft body 12 and stent 54 is disposed at the distal end. Stents located distally and proximally to a graft body provide structure and rigidity to the graft body. Additionally, proximal and distal stents may seal against the main vessel wall to prevent leakage around a branch vessel following perforation.

As shown in FIG. 2, stents are located at the proximal and distal ends of the graft body. Stents may seal against the main vessel wall 122 to prevent undesirable fluid leakage, for example by reducing blood leakage into an aneurysmal sac 121 spanned by an implanted graft body. Additional stents may further aid in sealing against the vessel wall 122 to prevent undesirable fluid leakage into the aneurysmal sac 121.

The stents may be self-expanding or balloon-expandable, and may be deployed according to conventional methodology, such as by an inflatable balloon catheter, by a self-deployment mechanism (after release from a catheter), or by other appropriate means. The stents may be bifurcated, configured for any blood vessel including coronary arteries and peripheral arteries (e.g., renal, superficial femoral, carotid, and the like), a urethral stent, a biliary stent, a tracheal stent, a gastrointestinal stent, or an esophageal stent, for example. Desirably, the stent is a vascular stent such as the commercially available Gianturco-Roubin FLEX-STENT®, GRII™, SUPRA-G, or V FLEX coronary stents from Cook Incorporated (Bloomington, Ind.).

The stents may be made of one or more suitable biocompatible materials such as stainless steel, nitinol, MP35N, gold, tantalum, platinum or platinum iridium, niobium, tungsten, iconel, ceramic, nickel, titanium, stainless steel/titanium composite, cobalt, chromium, cobalt/chromium alloys, magnesium, aluminum, or other biocompatible metals and/or composites or alloys such as carbon or carbon fiber, cellulose acetate, cellulose nitrate, silicone, cross-linked polyvinyl alcohol (PVA) hydrogel, cross-linked PVA hydrogel foam, polyurethane, polyamide, styrene isobutylene-styrene block copolymer (Kraton), polyethylene teraphthalate, polyester, polyorthoester, polyanhydride, polyether sulfone, polycarbonate, polypropylene, high molecular weight polyethylene, polytetrafluoroethylene, or other biocompatible polymeric material, or mixture of copolymers thereof; polyesters such as, polylactic acid, polyglycolic acid or copolymers thereof, a polyanhydride, polycaprolactone, polyhydroxybutyrate valerate or other biodegradable polymer, or mixtures or copolymers thereof; extracellular matrix components, proteins, collagen, fibrin or other therapeutic agent, or mixtures thereof. Desirably, the stents comprise stainless steel or nitinol.

Radiopacity

The graft body may be marked for radiographic visualization to facilitate precise alignment within the aortic artery with the particular branch anatomical conduit (e.g., carotid, innominate, subclavian, intercostal, superior mesenteric, celiac, renal, iliac, hypogastric, or visceral vessels). Radiopaque portions of the graft body would be seen by remote imaging methods including X-ray, ultrasound, Magnetic Resonance Imaging and the like, or by detecting a signal from or corresponding to the marker.

In other embodiments, the delivery device can comprise indicia relating to the orientation of the frame within the body vessel. In other embodiments, indicia can be located, for example, on a portion of a delivery catheter that can be correlated to the location of the prosthesis within a body vessel.

Radiopaque materials may be added to the graft body by any fabrication method or absorbed into or sprayed onto the surface of part or all of the graft. The degree of radiopacity contrast can be altered by implant content. Common radiopaque materials include barium sulfate, bismuth subcarbonate, and zirconium dioxide. Other radiopaque elements include: cadmium, tungsten, gold, tantalum, bismuth, platium, iridium, and rhodium. Radiopacity is typically determined by fluoroscope or x-ray film.

Attachment of Graft Device in Body Vessel

Prostheses according to the present invention may optionally include supplemental attachment means such as anchoring members, suturing, stapling, searing, bonding, gluing, bioadhesives, or otherwise adhering the medical device to the vessel wall or combinations thereof. For example, the graft body may be secured in place with one or more anchoring devices.

The art provides a wide variety of structural features that are acceptable for use in medical devices as anchoring members, and any suitable structural feature can be used. For example, individual barbs may be used to implant the graft body into a body vessel. The barbs may be secured to the graft body by any means known to one skilled in the art, including but not limited to welding to included stents, stitching, bonding, and adhesives. Desirably, barbs may be attached to stents included in the prosthesis. In some embodiments, the number, arrangement, and configuration of barbs can vary according to design preference and the clinical use of the graft body. The barbs can have any suitable shape, including points or "fish hook"-like configurations. The barbs may or may not penetrate the vessel wall, depending on their design and other factors.

Alternatively or in addition to anchoring members, bioadhesives may be used for attachment. Bioadhesive may be included in any suitable part of the prosthesis. Preferably, the bioadhesive is attached to the abluminal surface of the graft body. Selection of the type of bioadhesive, the portions of the prosthesis comprising the bioadhesive, and the manner of attaching the bioadhesive to the prosthesis can be chosen to perform a desired function upon implantation. For example, the bioadhesive can be selected to promote increased affinity of the desired portion of prosthesis to the section of the body vessel against which it is urged.

Bioadhesives for use in conjunction with the present invention include any suitable bioadhesives known to those of ordinary skill in the art. For example, appropriate bioadhesives include, but are not limited to, the following: (1) cyanoacrylates such as ethyl cyanoacrylate, butyl cyanoacrylate, octyl cyanoacrylate, and hexyl cyanoacrylate; (2) fibrinogen, with or without thrombin, fibrin, fibropectin, elastin, and laminin; (3) mussel adhesive protein, chitosan, prolamine gel and transforming growth factor beta (TGF-B); (4) polysaccharides such as acacia, carboxymethyl-cellulose, dextran, hyaluronic acid, hydroxypropyl-cellulose, hydroxypropyl-methylcellulose, karaya gum, pectin, starch, alginates, and tragacanth; (5) polyacrylic acid, polycarbophil, modified hypromellose, gelatin, polyvinyl-pylindone, polyvinylalcohol, polyethylene glycol, polyethylene oxide, aldehyde relative multifunctional chemicals, maleic anhydride co-polymers, and polypeptides; and (6) any bioabsorbable and biostable polymers derivatized with sticky molecules such as arginine, glycine, and aspartic acid, and copolymers.

Furthermore, commercially available bioadhesives that may be used in the present invention include, but are not limited to: FOCALSEAL® (biodegradable eosin-PEG-lactide hydrogel requiring photopolymerization with Xenon light wand) produced by Focal; BERIPLAST® produced by Adventis-Bering; VIVOSTAT® produced by ConvaTec (Bristol-Meyers-Squibb); SEALAGEN™ produced by Baxter; FIBRX® (containing virally inactivated human fibrinogen and inhibited-human thrombin) produced by CryoLife; TISSEEL® (fibrin glue composed of plasma derivatives from the last stages in the natural coagulation pathway where soluble fibrinogen is converted into a solid fibrin) and TISSUCOL® produced by Baxter; QUIXIL® (Biological Active Component and Thrombin) produced by Omrix Biopharm; a PEG-collagen conjugate produced by Cohesion (Collagen); HYSTOACRYL® BLUE (ENBUCRILATE) (cyanoacrylate) produced by Davis & Geck; NEXACRYL™ (N-butyl cyanoacrylate), NEXABOND™, NEXABOND™ S/C, and TRAUMASEAL™ (product based on cyanoacrylate) produced by Closure Medical (TriPoint Medical); DERMABOND® which consists of 2-octyl cyanoacrylate produced as DERMABOND® by (Ethicon); TISSUEGLU® produced by Medi-West Pharma; and VETBOND® which consists of n-butyl cyanoacrylate produced by 3M.

Bioactive Agents

Optionally, the graft body can include at least one bioactive agent or second agent compatible with the first agent discussed above. The second agent can be included in any suitable part of the prosthesis. The bioactive materials can be attached to the prosthesis in any suitable manner. For example, a bioactive agent may be sprayed onto the graft body material, or stents may be dipped in bioactive agent. Selection of the type of bioactive agent, the portions of the prosthesis comprising the bioactive agent, and the manner of attaching the bioactive agent to the prosthesis can be chosen to perform a desired function upon implantation. For example, the bioactive material can be selected to treat indications such as coronary artery angioplasty, renal artery angioplasty, carotid artery surgery, renal dialysis fistulae stenosis, or vascular graft stenosis. It is understood that the first agent may be the same or different compound as the second agent.

The second agent can be selected to perform one or more desired biological functions. For example, the abluminal surface of the graft body can comprise a bioactive selected to promote the ingrowth of tissue from the interior wall of a body vessel, such as a growth factor. An anti-angiogenic or antineoplastic bioactive such as paclitaxel, sirolimus, or a rapamycin analog, or a metalloproteinase inhibitor such as batimastat can be incorporated in or coated on the prosthesis to mitigate or prevent undesired conditions in the vessel wall, such as restenosis. Many other types of bioactive agents can be incorporated in the prosthesis.

Bioactive materials for use in biocompatible coatings include those suitable for coating an implantable medical device. The bioactive agent can include, for example, one or more of the following: antiproliferative agents (sirolimus, paclitaxel, actinomycin D, cyclosporine), immunomodulating drugs (tacrolimus, dexamethasone), metalloproteinase inhibitors (such as batimastat), antisclerosing agents (such as collagenases, halofuginone), prohealing drugs (nitric oxide donors, estradiols), mast cell inhibitors and molecular interventional bioactive agents such as c-myc antisense compounds, thromboresistant agents, thrombolytic agents, antibiotic agents, anti-tumor agents, antiviral agents, antiangiogenic agents, angiogenic agents, anti-mitotic agents, anti-inflammatory agents, angiostatin agents, endostatin agents, cell cycle regulating agents, genetic agents, including hormones such as estrogen, their homologs, derivatives, fragments, pharmaceutical salts and combinations thereof. Other useful bioactive agents include, for example, viral vectors and growth hormones such as Fibroblast Growth Factor and Transforming Growth Factor-β.

Further examples of antithrombotic bioactive agents include anticoagulants such as heparin, low molecular weight heparin, covalent heparin, synthetic heparin salts, coumadin, bivalirudin (hirulog), hirudin, argatroban, ximelagatran, dabigatran, dabigatran etexilate, D-phenalanyl-L-poly-L-arginyl, chloromethy ketone, dalteparin, enoxaparin, nadroparin, danaparoid, vapiprost, dextran, dipyridamole, omega-3 fatty acids, vitronectin receptor antagonists, DX-9065a, Cl-1083, JTV-803, razaxaban, BAY 59-7939, and LY-51, 7717; antiplatelets such as eftibatide, tirofiban, orbofiban, lotrafiban, abciximab, aspirin, ticlopidine, clopidogrel, cilostazol, dipyradimole, nitric oxide sources such as sodium nitroprussiate, nitroglycerin, S-nitroso and N-nitroso compounds; fibrinolytics such as alfimeprase, alteplase, anistreplase, reteplase, lanoteplase, monteplase, tenecteplase, urokinase, streptokinase, or phospholipid encapsulated microbubbles; and other bioactive agents such as endothelial progenitor cells or endothelial cells.

Delivery of Graft Device

The graft device can be configured for delivery to a body vessel. For example, a prosthesis comprising a graft body and stents according to the present invention can be compressed to a delivery configuration within a retaining sheath that is part of a delivery system, such as a catheter-based system. Upon delivery, the prosthesis can be expanded, for example, by inflating a balloon from inside the stents. The delivery configuration can be maintained prior to deployment of the prosthesis by any suitable means, including a sheath, a suture, a tube or other restraining material around all or part of the compressed prosthesis, or other methods.

Prostheses can be deployed in a body vessel by means appropriate to their design. Prostheses of the present invention can be adapted for deployment using conventional methods known in the art and employing percutaneous transluminal catheter devices. The prostheses are designed for deployment by any of a variety of in situ expansion means.

In one embodiment, a prosthesis comprising self-expanding stents and a graft body of the present invention may be mounted onto a catheter that holds the prosthesis as it is delivered through the body lumen and then releases the prosthesis and allows it to self-expand into contact with the body lumen. This deployment is effected after the prosthesis has been introduced percutaneously, transported transluminally and positioned at a desired location by means of the catheter. The self-expanding prosthesis may be deployed according to well-known deployment techniques for self-expanding medical devices. For example, the prosthesis may be positioned at the distal end of a catheter with a removable sheath or sleeve placed over the prosthetic valve to hold the prosthesis in a contracted state with a relatively small diameter. The prosthesis may then be implanted at the point of treatment by advancing the catheter over a guide wire to the location of the lesion, aligning graft body within the aortic artery and with any branch vessels, and then withdrawing the sleeve from over the prosthesis. The stent graft will automatically expand and exert pressure on the wall of the blood vessel at the site of treatment. The catheter, sleeve, and guide wire may then be removed from the patient.

In some embodiments, a bioabsorbable suture or sheath can be used to maintain a self-expanding stent graft in a compressed configuration both prior to and after deployment. As the bioabsorbable sheath or suture is degraded by the body after deployment, the prosthesis can expand within the body vessel. In some embodiments, a portion of the prosthesis can be restrained with a bioabsorbable material and another portion allowed to expand immediately upon implantation. For example, a self-expanding stent graft can be partially restrained by a bioabsorbable material upon deployment and later expand as the bioabsorbable material is absorbed.

In another embodiment, a stent graft may be first positioned to surround a portion of an inflatable balloon catheter. The prosthesis, with the balloon catheter inside is configured at a first, collapsed diameter. The prosthesis and the inflatable balloon are percutaneously introduced into a body vessel, following a previously positioned guide wire. For example, in rapid exchange, a rapid exchange prosthesis delivery balloon catheter allows exchange from a balloon angioplasty catheter to a prosthesis delivery catheter without the need to replace the angioplasty catheter guide wire with an exchange-length wire guide before exchanging the catheters. The prosthesis may be tracked by a fluoroscope, until the balloon portion and associated prosthesis are positioned within the body passageway at the point where the prosthesis is to be placed. Thereafter, the balloon is inflated and the prosthesis is expanded by the balloon portion from the collapsed diameter to a second expanded diameter. After the prosthesis has been expanded to the desired final expanded diameter, the balloon is deflated, and the catheter may be withdrawn, leaving the prosthesis in place. The prosthesis may be covered by a removable sheath during delivery to protect both the prosthesis and the vessels.

While the present invention has been described in terms of preferred embodiments, it will be understood, of course, that the invention is not limited thereto since modifications may be made to those skilled in the art, particularly in light of the foregoing teachings.

The invention claimed is:

1. A method for making an implantable graft device having treated yarn, the method comprising: applying an agent on one of weft yarns and warp yarns, wherein at least one of the warp yarns and the weft yarns comprises at least a first strand and a second strand, one of the first strand or one of the second strand comprising the agent applied thereto and the first strand and second strand being combined together to define one of the weft yarns and the warp yarns; drying the one of the weft and warp yarns; and after applying, interlacing the warp yarns in a first direction with the weft yarns in a second direction to define a graft body having a lumen defining a longitudinal axis and comprising proximal and distal ends.

2. The method of claim 1 wherein applying the agent is completed by one of the following processes:
dipcoating, spray coating, plasma deposition, chemical vapor deposition, vapor deposition, and chemical attachment.

3. The method of claim 1 wherein the agent is one of an anti-microbial agent, antibiotic agent, and an antithrombogenic agent.

4. The method of claim 1 wherein the graft body includes an anchor portion extending from the proximal end thereof, the anchor portion having a first woven portion comprised of woven yarn, and wherein the graft body includes an end portion extending from the distal end thereof, the end portion having a second woven portion comprised of woven yarn.

5. The method of claim 1 wherein the one of the first strand and the second strand is the first strand comprising the agent applied thereto.

6. The method of claim 4 further comprising:
disposing an expandable stent circumferentially on the graft body and about the longitudinal axis, defining the implantable graft device;
attaching a barb stent to the anchor portion for reduced migration of the graft device; and
attaching an end stent to the end portion.

7. The method of claim 6 wherein the graft body comprises an inner side and an outer side, the at least one expandable stent being attached to the inner side of the graft body.

8. The method of claim 6 wherein the first woven portion comprises an inner side, the barb stent being attached to the inner side of the first woven portion.

9. The method of claim 8 wherein the barb stent comprises a plurality of loops attached to the first woven portion.

10. A method for making an implantable graft device having treated yarn, the method comprising:

applying an agent on one of weft yarns and warp yarns, wherein at least one of the warp yarns and the weft yarns comprises at least a first strand and a second strand, one of the first strand and second strand comprising the agent applied thereto and the first strand and second strand being combined together to define one of the weft yarns and the warp yarns, wherein the one of the first strand and the second strand is the first strand comprising the agent applied thereto;

drying the one of the weft and warp yarns; and after applying, interlacing the warp yarns in a first direction with the weft yarns in a second direction to define a graft body having a lumen defining a longitudinal axis and comprising proximal and distal ends.

* * * * *